(12) United States Patent
Kim (10) Patent No.: US 8,628,951 B2
(45) Date of Patent: *Jan. 14, 2014

(54) LAB-ON-A-CHIP AND METHOD OF DRIVING THE SAME

(75) Inventor: Hye Yoon Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 407 days.

This patent is subject to a terminal disclaimer.

(21) Appl. No.: 12/893,898

(22) Filed: Sep. 29, 2010

(65) Prior Publication Data

US 2011/0151475 A1 Jun. 23, 2011

(30) Foreign Application Priority Data

Dec. 18, 2009 (KR) .................. 10-2009-0126776

(51) Int. Cl.
*C12M 1/34* (2006.01)

(52) U.S. Cl.
USPC ...................................... 435/287.1

(58) Field of Classification Search
None
See application file for complete search history.

(56) References Cited

U.S. PATENT DOCUMENTS

| | | | | |
|---|---|---|---|---|
| 3,846,903 | A * | 11/1974 | Rupert et al. | 228/200 |
| 5,458,852 | A * | 10/1995 | Buechler | 422/417 |
| 7,238,325 | B2 | 7/2007 | Anazawa et al. | |
| 8,394,595 | B2 | 3/2013 | Jung et al. | |
| 2008/0196483 | A1 | 8/2008 | Kurt et al. | |
| 2010/0227419 | A1* | 9/2010 | Jung et al. | 436/518 |
| 2011/0000561 | A1 | 1/2011 | Asogawa et al. | |

FOREIGN PATENT DOCUMENTS

| | | | |
|---|---|---|---|
| JP | 62-196624 A | 8/1987 | |
| JP | 3531941 B2 | 3/2004 | |
| JP | 2005-534044 A | 11/2005 | |
| JP | 2009-501928 A | 1/2009 | |
| JP | 2009-516844 A | 4/2009 | |
| KR | 10-2003-0038739 A | 5/2003 | |
| KR | 1020040043897 A | 5/2004 | |
| KR | 1020090006607 A | 1/2009 | |
| KR | 10-2009-0039130 B1 | 4/2009 | |
| KR | 1020090039130 A | 4/2009 | |
| KR | 1020090064935 A | 6/2009 | |
| KR | 1020090088085 A | 8/2009 | |
| WO | WO 98/43739 A2 | 10/1998 | |
| WO | WO 2004/011147 A1 | 2/2004 | |
| WO | WO 2007/060523 A1 | 5/2007 | |
| WO | WO 2009/051432 * | 4/2009 | G01N 33/49 |
| WO | WO 2009/051432 A2 | 4/2009 | |
| WO | WO 2009/119698 A1 | 10/2009 | |

* cited by examiner

*Primary Examiner* — N. C. Yang
*Assistant Examiner* — Richard Moerschell (57) ABSTRACT

Provided are a lab-on-a-chip and a method of driving the same. The lab-on-a-chip includes a first region where a lower substrate and an upper substrate are bonded to each other, a second region where the lower and upper substrates are not bonded to each other, a gap control member disposed at a terminal of the second region facing an interface between the first and second regions, and configured to control a gap between the lower and upper substrates at the terminal of the second region, and a pressure application member disposed at the terminal of the second region facing the interface between the first and second regions, and configured to apply pressure to the upper substrate at the terminal of the second region to reduce a gap between the lower and upper substrates in the center of the second region. Thus, binding events between a fluid sample to be analyzed and a reagent can be maximized so that a high signal can be obtained using only an infinitesimal quantity of sample.

4 Claims, 7 Drawing Sheets

LAB-ON-A-CHIP AND METHOD OF DRIVING THE SAME

CROSS-REFERENCE TO RELATED APPLICATION

This application claims priority to and the benefit of Korean Patent Application No. 10-2009-0126776, filed Dec. 18, 2009, the disclosure of which is incorporated herein by reference in its entirety.

BACKGROUND

1. Field of the Invention

The present invention relates to a lab-on-a-chip and, more particularly, to a lab-on-a-chip for controlling a capillary force and a method of driving the same.

2. Discussion of Related Art

The development of human society has led to ceaseless development of chemistry-related industries, which involves the development of chemical analysis techniques. A chemical analysis technique commonly refers to a method of discerning and detecting materials, and finding the chemical compositions of the materials.

In order to make a rapid and accurate chemical analysis, development of a chemical analysis apparatus for enabling an automatic chemical analysis instead of manual analysis by a researcher is under way. As long as a collected sample is supplied to the chemical analysis apparatus, the chemical analysis apparatus may, in a single measurement system, automatically blend the sample with reagents, allow the sample to react with the reagent for a predetermined amount of time, transport a reactant to a detector, and output an electrical or optical signal in proportion to the concentration of a target to be measured.

In recent years, a new apparatus obtained by finely embodying the automatic analysis apparatus in a subminiature chip has been developed and is called a lab-on-a-chip.

A lab-on-a-chip is a device that enables lab experiments using a subminiature chip into which hyperfine-circuit semiconductor technology, nano-technology, and bio-engineering technology are integrated. The lab-on-a-chip may accelerate an experimental research process using only an infinitesimal quantity of sample. The lab-on-a-chip is a bio-chip that is being developed as a diagnosis/analysis device in various fields, such as medical and bio-engineering fields.

Since a lab-on-a-chip has a fine fluid channel, while guiding a fluid sample to the channel, various manipulations, such as mixtures and reactions of the fluid sample with reagents and detections of the fluid sample, may be performed to make a chemical analysis. When the chemical analysis is made using the lab-on-a-chip, a chemical analysis process may be greatly simplified. Also, a lab-on-a-chip used once is discarded and a new lab-on-a-chip is used. Thus, pre- and post-processing processes of the chemical analysis process may be omitted. A protein lab-on-a-chip used for analyzing and measuring a specific protein in the blood or a deoxyribonucleic-acid (DNA) lab-on-a-chip used for analyzing and measuring specific DNA in a sample is being put to practical use and widely used.

A conventional lab-on-a-chip may still enable an immune reaction due to a fluid change caused by capillary forces of upper and lower substrates and sidewalls and structures of the upper and lower substrates. However, an immune reaction, such as an antigen-antibody reaction, may be greatly affected by not only the capillary forces and the structures of the upper and lower substrates but also the height of a chip.

Accordingly, in order to obtain a high signal intensity using an infinitesimal quantity of sample, it is necessary to maximize binding events between a capture antibody planted in a lower substrate and a target antigen in the blood.

SUMMARY OF THE INVENTION

The present invention is directed to a lab-on-a-chip in which a gap between an upper substrate and a lower substrate is artificially reduced by applying pressure to the upper substrate to maximize binding events between a fluid sample to be analyzed and a reagent and a method of driving the lab-on-a-chip.

One aspect of the present invention is to provide a lab-on-a-chip including: a first region where a lower substrate and an upper substrate are bonded to each other; a second region where the lower and upper substrates are not bonded to each other; a gap control member disposed at a terminal of the second region facing an interface between the first and second regions, the gap control member configured to control a gap between the lower and upper substrates at the terminal of the second region; and a pressure application member disposed at the terminal of the second region facing the interface between the first and second regions, the pressure application member configured to apply pressure to the upper substrate at the terminal of the second region to reduce a gap between the lower and upper substrates in the center of the second region.

The lower substrate in the first region may include a filter unit and a first reaction unit.

The upper substrate in the first region may include a blood injection port.

The filter unit may filter blood corpuscles and allow blood plasma components to pass therethrough.

The first reaction unit may include a detection antibody, which reacts with blood plasma components to generate a first antigen-antibody reactant.

Both side portions of the lower and upper substrates in the second region may be exposed.

The lower substrate in the second region may include at least one second reaction unit.

The second reaction unit may include a capture antibody, which reacts with the first antigen-antibody reactant to generate a second antigen-antibody reactant.

The pressure application member may apply pressure to the upper substrate at the terminal of the second region to reduce a gap between the lower and upper substrates in the second reaction unit during a secondary antigen-antibody reaction of the first antigen-antibody reactant with the capture antibody.

The pressure application member may repetitively apply pressure to the upper substrate at the terminal of the second region.

The pressure application member may apply pressure to the upper substrate at the terminal of the second region at predetermined time intervals.

A portion of the gap control member may have a wedge shape interposed between the lower and upper substrates.

At least one of the lower and upper substrates may be a flexible substrate.

Another aspect of the present invention is to provide a method of driving a lab-on-a-chip including: preparing a lab-on-a-chip including a first region where a lower substrate and an upper substrate are bonded to each other and a second region where the lower and upper substrates are not bonded to each other; controlling a gap between the lower and upper substrates at a terminal of the second region corresponding to an interface between the first and second regions; and reducing a gap between the lower and upper substrates in the center of the second region by applying pressure to the upper substrate at the terminal of the second region corresponding to the interface between the first and second regions to control the flow of a fluid in the second region.

The flow of the fluid may include forward flow of the fluid from the first region to the second region, backward flow of the fluid from the second region to the first region, or stoppage of the fluid.

The second region may include at least one reaction unit. Controlling the flow of the fluid in the second region may include controlling a reaction of the fluid with the reaction unit.

Controlling the reaction of the fluid with the reaction unit may include applying pressure to the upper substrate at the terminal of the second region at predetermined time intervals.

BRIEF DESCRIPTION OF THE DRAWINGS

The above and other features and advantages of the present invention will become more apparent to those of ordinary skill in the art by describing in detail exemplary embodiments thereof with reference to the attached drawings in which:

FIGS. 7A through 8B are cross-sectional and side views illustrating the operation principle of a capillary lab-on-a-chip according to another exemplary embodiment of the present invention.

DETAILED DESCRIPTION OF EMBODIMENTS

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. Descriptions of well-known components and processing techniques are omitted so as not to unnecessarily obscure the embodiments of the present invention. Like reference numerals in the drawings denote like elements, and thus their description will be omitted.

It will be understood that when an element or layer is referred to as being "connected to" or "coupled to" another element or layer, it can be directly connected or coupled to the other element or layer or electrically connected or coupled to the other element or layer with intervening elements or layers therebetween.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof unless otherwise defined. Also, terms "portion," "unit," and "module" described in the specification may refer to units capable of processing at least one function or operation and be embodied through the use of hardware, software, or a combination of hardware and software.

Figure 1:
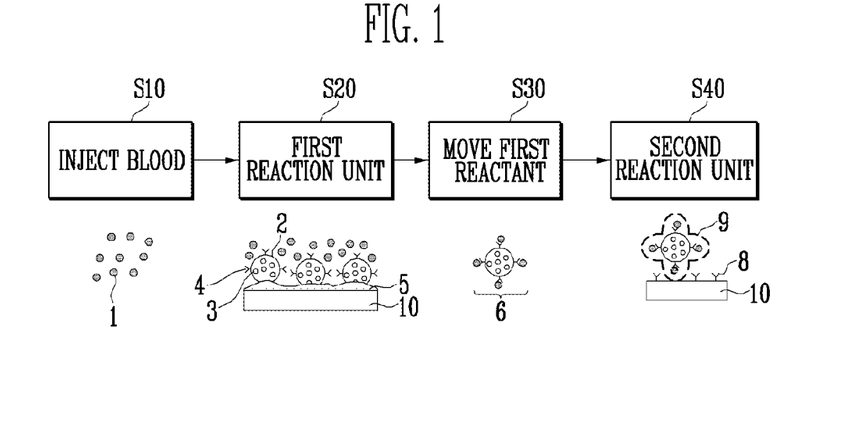
FIG. 1 is a flowchart illustrating a chemical analysis process in a lab-on-a-chip and conceptual diagrams thereof.

FIG. 1 is a flowchart illustrating a chemical analysis process in a lab-on-a-chip and conceptual diagrams thereof. A process of separating blood corpuscles from the blood and analyzing a specific protein (or antigen) contained in a portion of blood plasma components will be described as an example with reference to FIG. 1.

Referring to FIG. 1, the blood may be injected into the lab-on-a-chip in operation S10. A fluid containing biomarker protein 1 of the blood injected into the lab-on-a-chip may be moved to a first reaction unit.

The biomarker protein 1 contained in the fluid may react with carrier particles 2 containing a fluorescent substance 3 and a detection antibody 4 in operation S20. Each of the carrier particles 2 may have a size of several nm or μm. The carrier particles 2 may be attached to the lower substrate 10 in the first reaction unit using a scaffold 5 formed of a viscous liquid material with a good fastness characteristic. A primary antigen-antibody reaction may be caused between the biomarker protein 1 contained in the fluid and the detection antibody 4 contained in the carrier particles 2, thus generating a first antigen-antibody reactant (i.e., detection antigen-detection antibody composite 6).

The first antigen-antibody reactant 6 may be transported due to the flow of the fluid (S30). The first antigen-antibody reactant 6 transported due to the flow of the fluid may react with a capture antibody 8 in the second reaction unit. A secondary antigen-antibody reaction may be caused between the biomarker protein 1 included in the first antigen-antibody reactant 6 and the capture antibody 8 to generate a second antigen-antibody reactant 9. The second antigen-antibody reactant 9 may be irradiated with light to analyze a fluorescent image caused by the fluorescent substance 3 contained in the carrier particles 2 so that the absence or presence and content of a specific protein in the blood can be analyzed.

Figure 2A:
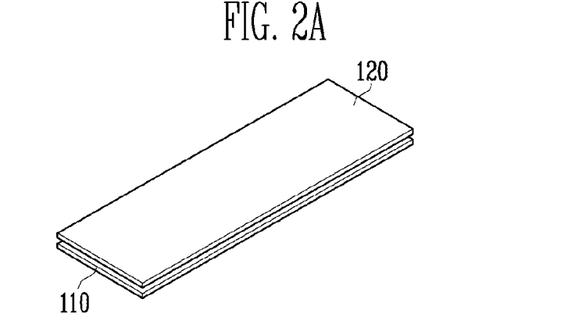
FIGS. 2A and 2B are conceptual perspective and cross-sectional views of a capillary lab-on-a-chip according to an exemplary embodiment of the present invention.
Figure 2B:
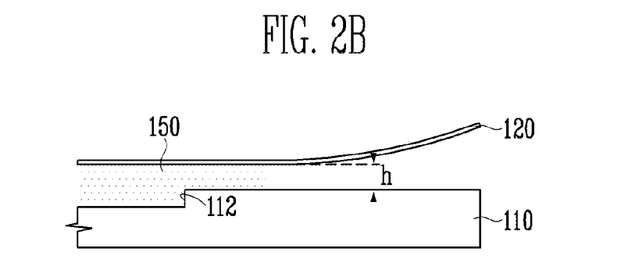

FIGS. 2A and 2B are conceptual perspective and cross-sectional views of a capillary lab-on-a-chip according to an embodiment of the present invention.

Referring to FIGS. 2A and 2B, the capillary lab-on-a-chip may include a lower substrate 110 and an upper substrate 120. The lower and upper substrates 110 and 120 may be spaced a predetermined distance "h" apart from each other to form a capillary tube. Opposing surfaces of the lower and upper substrates 110 and 120, which form the capillary tube, may have capillary forces.

As shown in FIG. 2A, even if both sidewalls of the capillary tube are exposed, a capillary phenomenon may occur. Although the capillary forces disappear at both of the exposed sidewalls of the capillary tube, the fluid sample 150 may have its own cohesion. In other words, since the capillary force is greater than the cohesion of the fluid sample 150 in the opposing surfaces of the lower and upper substrates 110 and 120 that form the capillary tube, the fluid sample 150 may flow along the opposing surfaces of the lower and upper substrates 110 and 120. However, since the capillary force disappears on the exposed sidewalls of the capillary tube, the fluid sample 150 cannot flow along the sidewalls of the capillary tube. Nevertheless, the fluid sample 150 cannot leak out of the exposed sidewalls of the capillary tube due to its cohesion.

Also, the capillary force in the opposing surfaces of the lower and upper substrates 110 and 120 that form the capillary tube is far greater than a capillary force at an interface between the exposed sidewalls of the lower and upper substrates 110 and 120. Therefore, the amount of the fluid sample 150 flowing along the interface between the exposed sidewalls of the lower and upper substrates 110 and 120 may be negligible.

The lower substrate 110 may include a filter unit 112. The filter unit 112 may filter unnecessary components of the fluid sample 50 and selectively allow only a specific component to be analyzed to pass therethrough. At least one of the lower and upper substrates 110 and 120 may be a flexible substrate having elasticity.

The upper substrate 120 may be a flexible substrate. Thus, when one end portion of the upper substrate 120 is lifted up, the upper substrate 120 may be bent in a curved shaped. That is, a region where a gap "h" is maintained between the lower and upper substrates 110 and 120 and a region where a gap greater than the gap "h" is maintained between the lower and upper substrates 110 and 120 may be formed.

Thus, the capillary force of the capillary tube formed by the lower and upper substrates 110 and 120 may be controlled. This will be described in further detail with reference to FIGS. 3A through 3E.

FIGS. 3A through 3E are conceptual cross-sectional views illustrating the operation principle of a capillary lab-on-a-chip according to an embodiment of the present invention.

Figure 3A:
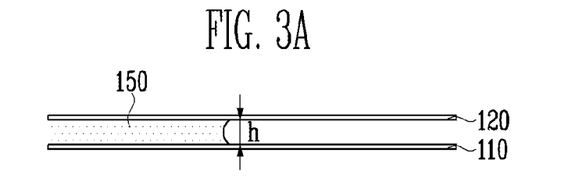
FIGS. 3A through 3E are conceptual sectional views illustrating the operation principle of a capillary lab-on-a-chip according to an exemplary embodiment of the present invention.

Referring to FIG. 3A, a channel of a capillary lab-on-a-chip may be a capillary tube in which the fluid sample 150 flows due to the capillary force caused by the gap "h" between the lower and upper substrates 110 and 120. Thus, when the gap "h" is maintained between the lower and upper substrates 110 and 120, the fluid sample 150 may keep flowing in the right direction along the capillary tube formed by the lower and upper substrates 110 and 120.

Figure 3B:
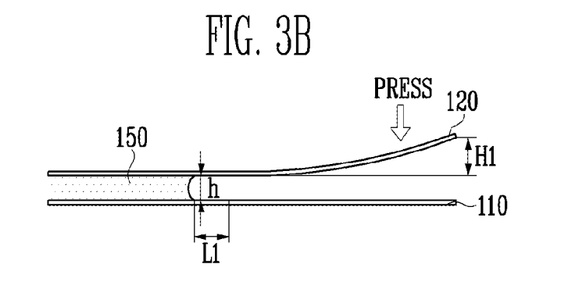

Referring to FIG. 3B, when the gap "h" is maintained between the lower and upper substrates 110 and 120 at one end portion of the capillary tube, the upper substrate 120 disposed at the other end portion of the capillary tube may be lifted up so that the gap "h" between the lower and upper substrates 110 and 120 may be increased to a gap "h+H1." Thus, the fluid sample 150 may flow a distance L1 backward. This is because the capillary tube has a threshold gap "h" to cause a capillary force. When the gap of the capillary tube is equal to or less than the threshold gap "h," the capillary tube may have the capillary force. Conversely, when the gap of the capillary tube is greater than the threshold gap "h," the capillary tube may lose the capillary force.

Figure 3C:
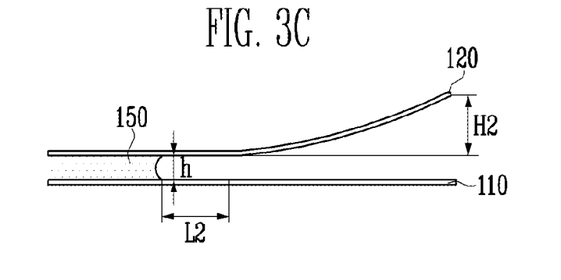

Referring to FIG. 3C, the upper substrate 120 disposed at the other end portion of the capillary tube may be further lifted up so that the gap "h+H1" between the lower and upper substrates 110 and 120 may be increased to a gap "h+H2," and the fluid sample 150 may further flow a distance of L2 backward.

Figure 3D:
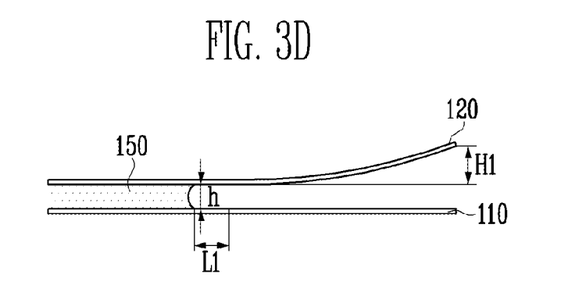

Referring to FIG. 3D, the upper substrate 120 disposed at the other end portion of the capillary tube may be dropped so that the gap "h+H2" between the lower and upper substrates 110 and 120 can be reduced to a gap "h+H1." Thus, the fluid sample 150 may flow a distance of L1 forward.

Figure 3E:
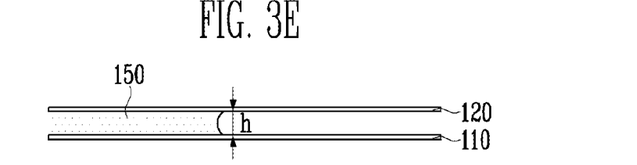

Referring to FIG. 3E, the upper substrate 120 disposed at the other end portion of the capillary tube may be further dropped so that the gap "h+H1" between the lower and upper substrates 110 and 120 can be further reduced to the gap "h." Thus, the fluid sample 150 may flow forward to the same spot as in FIG. 3A. Also, the fluid sample 150 may flow due to the capillary force of the capillary tube. In other words, the fluid sample 150 may keep flowing in the right direction along the capillary tube formed by the lower and upper substrates 110 and 120.

As can be seen from FIGS. 3A through 3E, a change in geometric shape of the capillary tube may lead to a change in the capillary force. Specifically, assuming that at least one of the lower and upper substrates 110 and 120 forming the capillary tube according to an embodiment of the present invention is a flexible substrate, the capillary force of the capillary tube may be controlled so that the flow of the fluid sample 150, for example, forward and backward flows and stoppage of the fluid sample 150, can be freely controlled.

When the fluid sample 150 reaches a desired position, the upper substrate 120 may be pushed with pressure using a pressure application unit, such as equipment, at a position "PRESS." As a result, a gap between the lower and upper substrates 110 and 120 of the lab-on-a-chip may be reduced to less than a gap "h" so that binding events between materials contained in the fluid sample 150 can be artificially increased, and the flow of the fluid sample 150 can be accelerated to increase reaction speed. Thus, the reaction efficiency of the materials contained in the fluid sample 150 may be increased.

For brevity, the position "PRESS" is illustrated only in FIG. 3B.

Figure 4:
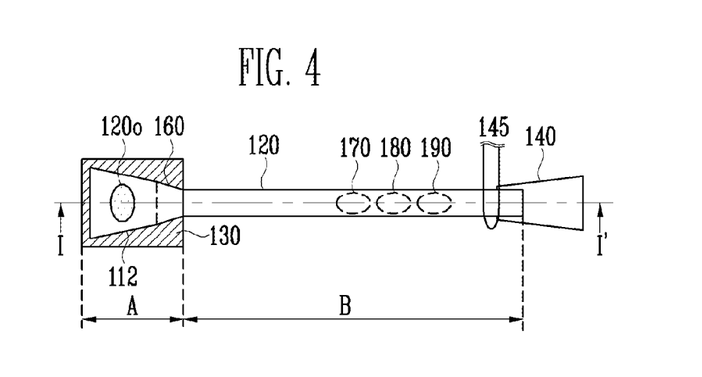
FIG. 4 is a plan view of a capillary lab-on-a-chip according to an exemplary embodiment of the present invention.

FIG. 4 is a plan view of a capillary lab-on-a-chip according to an embodiment of the present invention, and FIGS. 5A through 5G are cross-sectional views taken along line I-I' of FIG. 4. Hereinafter, a protein lab-on-a-chip for separating blood corpuscles from the blood and analyzing a specific protein contained in a portion of blood plasma components will be described as an example.

Figure 5A:
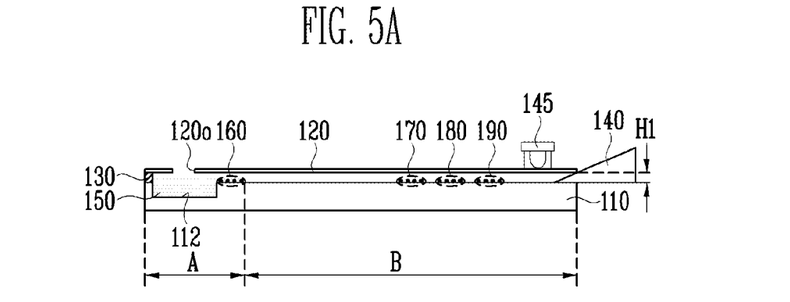
FIGS. 5A through 5G are cross-sectional views taken along line I-I' of FIG. 4.

Referring to FIGS. 4 and 5A, a capillary lab-on-a-chip may include a first region A where a lower substrate 110 and an upper substrate 120 are bonded to each other, a second region B wherein the lower and upper substrates 110 and 120 are not bonded to each other, and a gap control member 140 disposed at a terminal of the second region B facing an interface between the first and second regions A and B and configured to control the gap between the lower and upper substrates 110 and 120 at the terminal of the second region B, and a pressure application member 145 disposed at the terminal of the second region B facing the interface between the first and second regions A and B and configured to apply pressure to the upper substrate 120 at the terminal of the second region B and reduce a gap between the lower and upper substrates 110 and 120 in the center of the second region B.

The lower and upper substrates 110 and 120 in the first region A may be bonded to each other by a bonding member 130. The bonding member 130 may maintain the first region A airtight. The lower substrate 110 in the first region A may include a filter unit 112 and a first reaction unit 160.

A bottom surface of the filter unit 112 may be formed lower than a bottom surface of the first reaction unit 160 so that the filter unit 112 can serve as a fluid storage tank. The filter unit 112 may filter corpuscles of the blood 150 and allow a fluid containing blood plasma components to pass therethrough. The first reaction unit 160 may include detection antibodies (points 160 fixed to a fluorescent substance), which react with the blood plasma components of the blood 150 to generate a first antigen-antibody reactant (refer to 6 in FIG. 1).

The upper substrate 120 in the first region A may include a blood injection port 120o configured to inject the blood 150 therethrough. The corpuscles of the injected blood 150 may be filtered by the filter unit 112, and the fluid containing the blood plasma component may flow to the first reaction unit 160 due to capillary force of a capillary tube including the lower and upper substrates 110 and 120.

Both side portions of the lower and upper substrates 110 and 120 in the second region B may be exposed as described above with reference to FIGS. 2A and 2B. Also, by exposing both the side portions of the lower and upper substrates 110 and 120 in the second region B, the gap between the lower and upper substrates 110 and 120 may be controlled. The lower substrate 110 in the second region B may include at least one second reaction unit 170, 180, and/or 190.

The second reaction unit 170, 180, and/or 190 may include capture antibodies, which react with the first antigen-antibody reactant to generate second antigen-antibody reactants (refer to 9 in FIG. 1). The capture antibodies of the second reaction unit 170, 180, and/or 190 may cause respectively different antigen-antibody reactions. Analysis of various antigens may be made at the same time.

A portion of the gap control member 140 may be a wedge type interposed between the lower and upper substrates 110 and 120. The wedge-type gap control member 140 may move in the right and/or left direction between the lower and upper substrates 110 and 120 disposed at the terminal of the second region B so that the gap between the lower and upper substrates 110 and 120 at the terminal of the second region B may be freely controlled.

The pressure application member 145 may be any equipment capable of applying pressure to the upper substrate 120. The pressure application member 145, which is additional equipment, may apply pressure to the terminal of the second region B where the gap control member 140 is interposed (specifically, a front portion of the gap control member 140 or a portion of the terminal of the second region B close to the center thereof), thereby reducing a gap between the lower and upper substrates 110 and 120 in the center of the second region B where the second reaction unit 170, 180, and/or 190 is disposed.

Referring to FIG. 5A, a channel of a capillary lab-on-a-chip may be a capillary tube in which the blood 150 flows in the right direction due to the capillary force caused by the gap "H1" between the lower and upper substrates 110 and 120. Thus, when the gap "H1" is maintained between the lower and upper substrates 110 and 120, the blood 150 may keep flowing in the right direction along the capillary tube formed by the lower and upper substrates 110 and 120.

Figure 5B:
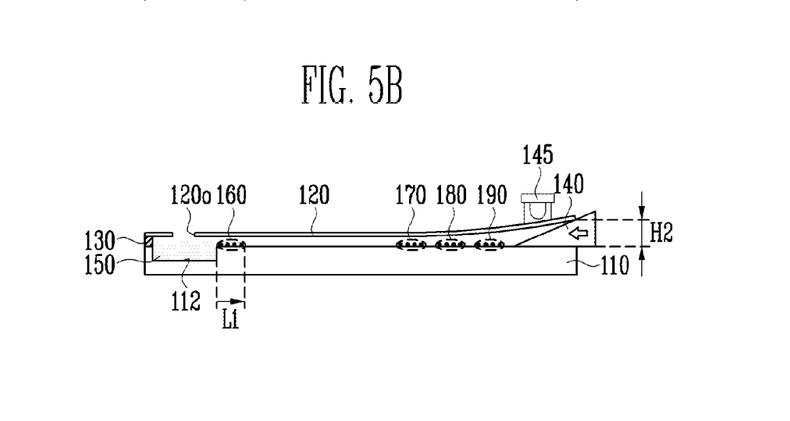

Referring to FIG. 5B, when the gap control member 140 moves in the left direction, the upper substrate 120 disposed at the terminal of the second region B may be lifted up so that the gap "H1" between the lower and upper substrates 110 and 120 may be increased to a gap "H2." Thus, a fluid (not shown) containing blood plasma components that flow to the second region B due to the capillary force may flow a distance of L1 backward to a region including the first reaction unit 160.

This may facilitate a primary antigen-antibody reaction between the blood plasma components contained in the fluid obtained by filtering the blood corpuscles of the blood 150 and the detection antibody of the first reaction unit 160.

As a result, a first antigen-antibody reactant (not shown) may be generated.

Figure 5C:
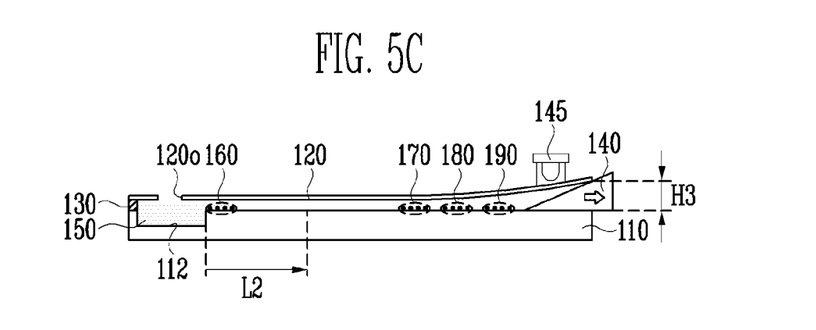

Referring to FIG. 5C, when the gap control member 140 moves in the right direction, the upper substrate 120 disposed at the terminal of the second region B may be dropped so that the gap "H2" between the lower and upper substrates 110 and 120 may be reduced to a gap "H3." Thus, a fluid containing the first antigen-antibody reactant and unreacted blood plasma components may flow a distance of L2 forward so that the first antigen-antibody generated by the first reaction unit 160 may be transported.

Figure 5D:
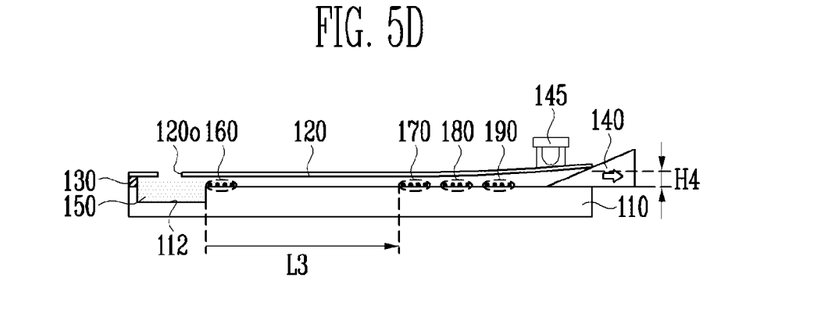

Referring to FIG. 5D, when the gap control member 140 further moves in the right direction, the upper substrate 120 disposed at the terminal of the second region B may be further dropped so that the gap "H3" between the lower and upper substrates 110 and 12 may be further reduced to a gap "H4." Thus, the fluid containing the first antigen-antibody reactant and the unreacted blood plasma components may further flow a distance of L3 forward. In order to generate the first antigen-antibody using the unreacted blood plasma components contained in the fluid, the process operations of FIGS. 5B through 5D may be repeated.

Figure 5E:
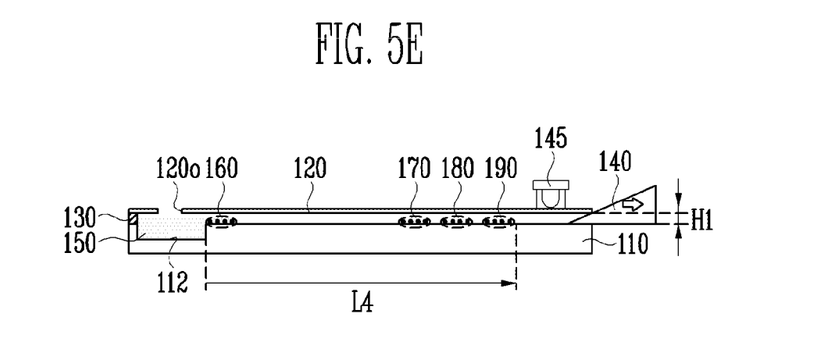

Referring to FIG. 5E, when the gap control member 140 moves in the right direction, the upper substrate 120 at the terminal of the second region B may be completely dropped so that a gap between the lower and upper substrates 110 and 120 may be completely reduced from H4 to H1. As a result, a fluid containing a first antigen-antibody reactant and an unreacted blood plasma component may flow a distance of L4 forward to a region including the second reaction unit 170, 180, and/or 190.

This may facilitate a secondary antigen-antibody reaction between the first antigen-antibody reactant generated by the first reaction unit 160 and the capture antibody of the second reaction unit 170, 180, and/or 190. Thus, a second antigen-antibody reactant (not shown) may be generated.

In this case, when the pressure application member 145 applies pressure to the upper substrate 120 to reduce a gap between the lower and upper substrates 110 and 120 to a value lower than H1, binding events of the secondary antigen-antibody reaction may be artificially increased.

The secondary antigen-antibody reaction will now be described in further detail.

The fluid containing the first antigen-antibody reactant and the unreacted blood plasma component may move forward to the region including the second reaction unit 170, 180, and/or 190 so that the secondary antigen-antibody may occur between the primary antigen-antibody generated by the first reaction unit 160 and the capture antibody of the second reaction unit 170, 180, and/or 190.

When the fluid containing the first antigen-antibody and the unreacted blood plasma components sufficiently reacts with the capture antibody of the second reaction unit 170, 180, and/or 190, preferably, though not necessarily, when the fluid reaches an intermediate portion of each of a plurality of second reaction units 170, 180, and/or 190, the pressure application member 145 applies pressure to the upper substrate 120 so that the gap between the lower and upper substrates 110 and 120, preferably, though not necessarily, a gap between the lower and upper substrates 110 and 120 in a region where the secondary antigen-antibody reaction occurs can be reduced. Thus, the first antigen-antibody reactant may move downward, so that binding events between the first antigen-antibody reactant and the capture antibody of the second reaction unit fixed to the lower substrate 110 can be further increased, and the flow of the fluid can be increased to increase reaction speed. As a result, the efficiency of the second antigen-antibody may be enhanced.

In order to further increase reaction efficiency, the pressure application member 145 may repetitively apply pressure to the upper substrate 120 when the fluid reaches an intermediate portion of each of a plurality of second reaction units 170, 180, and/or 190. Specifically, pressure may be repetitively applied to the upper substrate 120 at predetermined time intervals. The time intervals may be experimentally determined to maximize the efficiency of the secondary antigen-antibody reaction.

In the lab-on-a-chip according to the embodiment of the present invention, the upper substrate 120 may be a flexible substrate. Since the flexible substrate is thin and flexible, even if the pressure application member 145 disposed at the terminal of the upper substrate 120 applies pressure, a gap between the lower and upper substrates 110 and 120 in a region where the secondary antigen-antibody reaction occurs may be reduced.

Figure 5F:
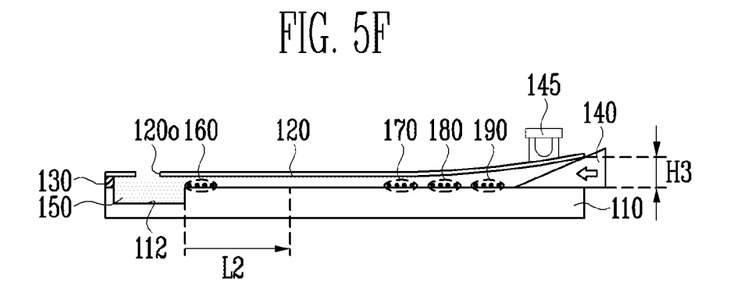

Referring to FIG. 5F, when the gap control member 140 moves in the left direction, the upper substrate 120 at the terminal of the second region B may be lifted up again so that the gap between the lower and upper substrates 110 and 120 may be increased again from H1 to H3. Thus, the fluid containing the second antigen-antibody reactant, the unreacted first antigen-antibody reactant, and the unreacted blood plasma component may flow a distance of L2 backward again.

Figure 5G:
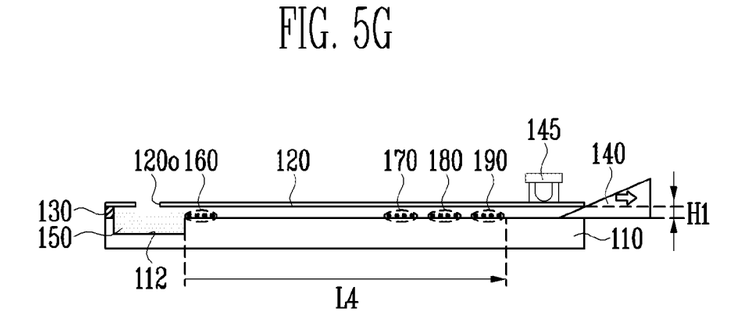

Referring to FIG. 5G, when the gap control member 140 moves in the right direction, the upper substrate 120 at the terminal of the second region B may be dropped again so that the gap between the lower and upper substrates 110 and 120 may be reduced again from H3 to H1. Thus, the fluid containing the secondary antigen-antibody, the unreacted first antigen-antibody reactant, and unreacted blood plasma components may flow a distance of L4 forward again.

This may facilitate a secondary antigen-antibody reaction between the first antigen-antibody reactant and the capture antibody of the second reaction unit 170, 180, and/or 190. The process operations of FIGS. 5E through 5G may be repeated in order to generate a second antigen-antibody reactant using the unreacted first antigen-antibody reactant contained in the fluid.

When the gap "H1" is continuously maintained between the lower and upper substrates 110 and 120 disposed at the terminal of the second region B, the fluid containing the unreacted blood plasma components and the unreacted first antigen-antibody may flow due to the capillary force of the capillary tube.

Also, repetition of the process operations of FIGS. 5E through 5G may lead to detachment of non-specific bonding components, thereby reducing noise signals generated during an analysis process. Since a conventional lab-on-a-chip cannot originally shift the direction of a fluid, completely detaching the non-specific bonding components is impossible. Furthermore, the detachment of the non-specific bonding components may be greatly affected by the motion speed of the fluid. The conventional capillary lab-on-a-chip may not control the motion speed but delay the flow of the fluid. However, unlike the conventional capillary lab-on-a-chip, the capillary lab-on-a-chip according to the present invention may minimize the noise signals generated during the analysis process.

As can be seen from FIGS. 5A through 5G, the number of times the fluid containing the blood plasma components flows, for example, the number of times the fluid flows forward, flows backward, or stops flowing may be controlled if required. Thus, time taken to allow the fluid containing the blood plasma components of the blood 150 to be analyzed to react with capture antibodies of the first and second reaction units 160, 170, 180, and/or 190 may be freely controlled.

Figure 6:
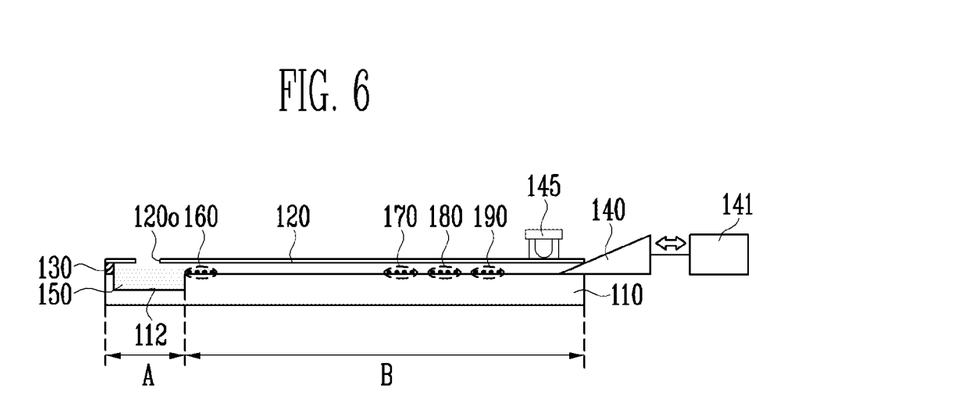
FIG. 6 is a cross-sectional view of a capillary lab-on-a-chip according to an exemplary embodiment of the present invention.

FIG. 6 is a cross-sectional view of a capillary lab-on-a-chip according to an embodiment of the present invention.

Referring to FIG. 6, a portion of a gap control member 140 of the capillary lab-on-a-chip may be formed as a wedge type interposed between a lower substrate 110 and an upper substrate 120. The wedge-type gap control member 140 may be moved in right and/or left directions between the lower and upper substrates 110 and 120 at a terminal of a second region B due to the drive of a step motor 141 to freely control a gap between the lower and upper substrates 110 and 120 at the terminal of the second region B.

Specifically, the capillary force of a capillary tube may be controlled by the wedge-type gap control member 140 due to the drive of the step motor 141 so that the flow of a fluid sample 150, for example, the forward and backward flows and stoppage of the fluid sample 150, may be freely controlled. Thus, time taken for a reaction of the fluid sample 150 to be analyzed with a reagent may be freely controlled.

Also, when the pressure application member 145 applies pressure to the upper substrate 120 to further reduce the gap between the lower and upper substrates 110 and 120, binding events (i.e., secondary antigen-antibody reactions) between materials contained in the fluid sample 150 may be artificially increased and the flow of the fluid sample 150 can be accelerated.

FIGS. 7A through 8B are cross-sectional and side views illustrating the operation principle of a capillary lab-on-a-chip according to another embodiment of the present invention.

Figure 7A:
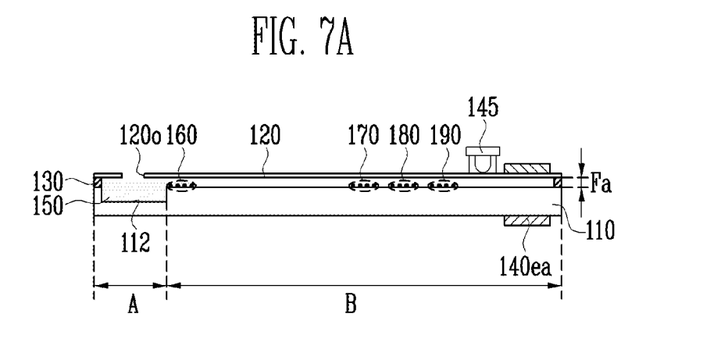
Figure 7B:
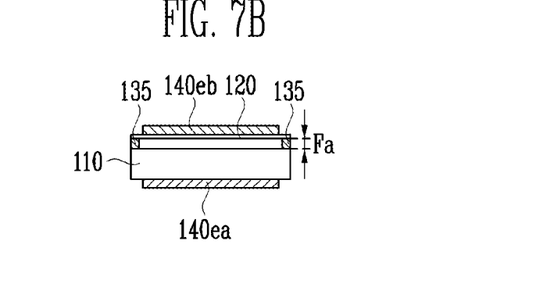

Referring to FIGS. 7A and 7B, gap control members 140*ea* and 140*eb* of a capillary lab-on-a-chip may be a pair of electromagnets, which are respectively provided on lower and upper substrates 110 and 120 disposed at a terminal of a second region B and face a gap between the lower and upper substrates 110 and 120. A support member 135 configured to maintain the minimum gap between the lower and upper substrates 110 and 120 at the terminal of the second region B may be further provided between the lower and upper substrates 110 and 120 disposed at the terminal of the second region B. The support member 135 may prevent the lower and upper substrates 110 and 120 forming a capillary tube from contacting each other.

When an attractive force Fa interacts between the pair of electromagnets functioning as the gap control members 140*ea* and 140*eb*, a gap between the lower and upper substrates 110 and 120 disposed at the terminal of the second region B may be reduced.

Figure 8A:
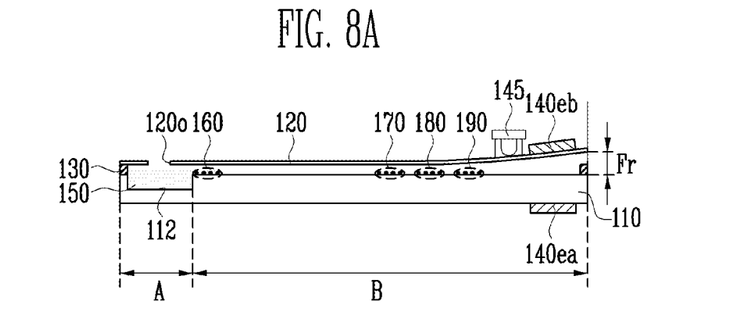
Figure 8B:
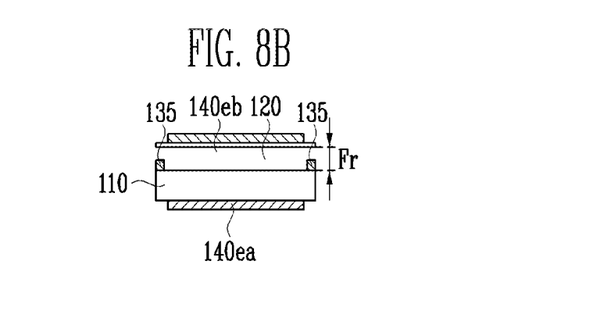

Referring to FIGS. 8A and 8B, a repulsive force Fr interacts between the pair of electromagnets functioning as the gap control members 140*ea* and 140*eb*, and the gap between the lower and upper substrates 110 and 120 disposed at the terminal of the second region B may be increased.

The attractive force Fa or repulsive force Fr may interact between the pair of electromagnets in the direction of current supplied to the pair of electromagnets.

Also, the intensities of attractive and repulsive forces caused between the pair of electromagnets may be controlled according to the current supplied to the pair of electromagnets. That is, the capillary force of the capillary tube may be controlled by the pair of electromagnets functioning as the gap control members 140*ea* and 140*eb* so that the flow of the fluid sample 150, for example, forward and backward flows and stoppage of the fluid sample 150, may be freely finely controlled. Thus, time taken for a reaction between the fluid sample 150 to be analyzed and a reagent may be freely controlled.

Furthermore, when the pressure application member 145 applies pressure to the upper substrate 120 to further reduce the gap between the lower and upper substrates 110 and 120, binding events between materials contained in the fluid sample 150 may be artificially increased, and the flow of the fluid sample 150 may be accelerated.

A capillary lab-on-a-chip according to embodiments of the present invention may be structured to artificially control a gap between upper and lower substrates forming a capillary tube, thereby freely and finely controlling the flow of a fluid. As a result, binding events between a fluid sample to be analyzed and a reagent may be increased so that a highly efficient capillary lab-on-a-chip having a signal amplification effect and a method of driving the lab-on-a-chip can be provided.

Figure 9A:
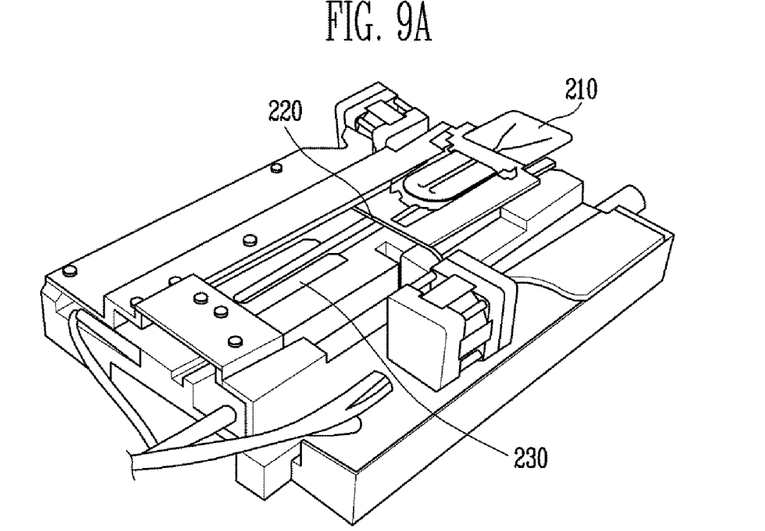
FIGS. 9A through 9C are perspective and plan views of a driver including a capillary lab-on-a-chip according to an exemplary embodiment of the present invention.
Figure 9B:
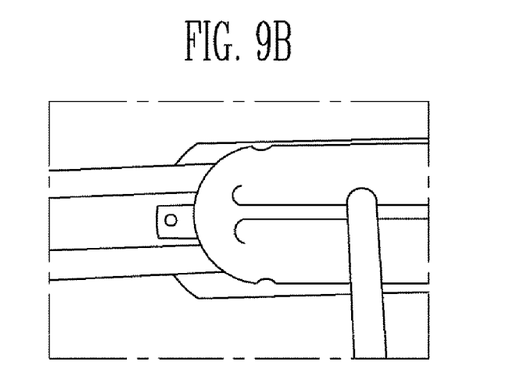
Figure 9C:
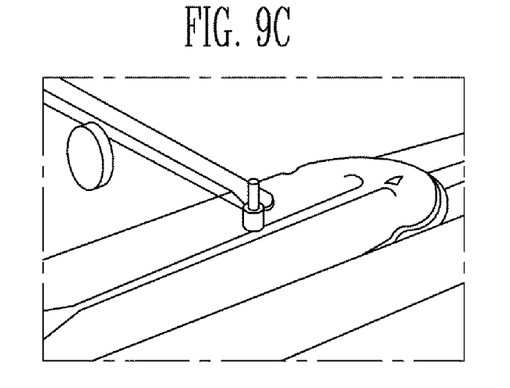

FIGS. 9A through 9C are perspective and plan views of a driver including a capillary lab-on-a-chip according to an embodiment of the present invention.

Referring to FIGS. 9A through 9C, the driver according to the embodiment of the present invention may include a lab-oh-a-chip 210, a reaction control unit 220, and a wedge-type structure 230.

The wedge-type structure 230 functioning as a gap control member may be inserted into an end portion of the lab-on-a-chip 210, and equipment functioning as a pressure application member may be mounted in the center of the lab-on-a-chip 210 to apply pressure to an upper substrate of the lab-on-a-chip 210.

Although it is illustrated that the pressure application member is mounted in the center of the lab-on-a-chip 210, the pressure application member may move in a horizontal direction along the lab-on-a-chip 210. According to an embodiment of the present invention, when the pressure application member applies pressure to the upper substrate of the lab-on-a-chip 210, after the pressure application member is moved to a front portion of the wedge-type structure 230, that is, the end portion of the lab-on-a-chip 210 in which the wedge-type structure 230 is mounted, the pressure may be applied to the upper substrate.

The reaction control unit 220 may function to control the whole operation of the lab-on-a-chip 210.

By use of the above-described driver including the capillary lab-on-a-chip, binding events (i.e., secondary antigen-antibody reactions) between materials contained in a fluid injected into the capillary lab-on-a-chip may be maximized.

According to embodiments of the present invention, pressure may be applied to an upper substrate using arbitrary equipment so that a gap between the upper substrate and a lower substrate can be artificially reduced so that binding events between a fluid sample to be analyzed and a reagent can be maximized.

Specifically, binding events between an antigen and an antibody that participate in an immune reaction, that is, secondary antigen-antibody reactions between a first antigen-antibody reactant and a capture antibody, can be maximized so that a high signal can be obtained using an infinitesimal quantity of sample.

In the drawings and specification, there have been disclosed typical preferred embodiments of the invention and, although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

What is claimed is:

1. A method of driving a lab-on-a-chip, comprising:
preparing a lab-on-a-chip including a first region where a lower substrate and an upper substrate are bonded to each other and a second region where the lower and upper substrates are not bonded to each other, the second region including a gap provided between the lower and upper substrates, the gap having a first distance between the lower substrate and the upper substrate after the lab-on-a-chip is prepared;
controlling the gap between the lower and upper substrates at a terminal region of the second region using a gap control member so that the gap has a distance greater than the first distance to control a flow of a fluid in the second region, the terminal region of the second region opposing an interface between the first and second regions; and
reducing the gap between the lower and upper substrates using a pressure application member so that the gap has a second distance less than the first distance in a center region of the second region by applying pressure to a portion of the upper substrate in the terminal region of the second region to control a reaction of the fluid in the second region.

2. The method of claim 1, wherein the flow of the fluid comprises any of forward flow of the fluid from the first region to the second region, backward flow of the fluid from the second region to the first region, and stoppage of the fluid.

3. The method of claim 1, wherein the second region comprises at least one reaction unit, and
wherein reducing the distance of the gap to control the reaction of the fluid in the second region comprises controlling a reaction of the fluid in the reaction unit.

4. The method of claim 3, wherein reducing the distance of the gap to control the reaction of the fluid in the reaction unit comprises applying pressure to the portion of the upper substrate in the terminal region of the second region at predetermined time intervals.

* * * * *